US007967787B2

(12) United States Patent

Nagata et al.

(10) Patent No.: US 7,967,787 B2

(45) **Date of Patent: *Jun. 28, 2011**

(54) GASTROSTOMY TUBE EXTENSION DEVICE

(75) Inventors: Katsuki Nagata, Fukuroi (JP); Yasuyuki Baba, Fukuroi (JP)

(73) Assignee: Tyco Healtcare Group LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/631,835

(22) PCT Filed: Apr. 26, 2005

(86) PCT No.: PCT/EP2005/004464

§ 371 (c)(1), (2), (4) Date: Jan. 4, 2008

(87) PCT Pub. No.: WO2005/105017

PCT Pub. Date: Nov. 10, 2005

(65) Prior Publication Data

US 2008/0208208 A1 Aug. 28, 2008

(30) Foreign Application Priority Data

Apr. 30, 2004 (JP) ................................ 2004-135258

(51) Int. Cl.
*A61M 5/178* (2006.01)

(52) U.S. Cl. .................................................. 604/164.04

(58) Field of Classification Search ............... 604/96.01, 604/27, 506, 117, 164.04, 513

See application file for complete search history.

(56) References Cited

U.S. PATENT DOCUMENTS

| | | | | |
|---|---|---|---|---|
| 3,261,357 | A * | 7/1966 | Roberts et al. | 604/105 |
| 3,397,699 | A | 8/1968 | Kohl | |
| 4,861,334 | A | 8/1989 | Nawaz | |
| 5,073,166 | A | 12/1991 | Parks et al. | |
| 5,080,650 | A | 1/1992 | Hirsch et al. | |
| 5,792,119 | A * | 8/1998 | Marx | 604/247 |
| 5,855,569 | A | 1/1999 | Komi | |
| 5,989,225 | A * | 11/1999 | Bodicky et al. | 604/174 |
| 6,231,549 | B1 | 5/2001 | Noecker et al. | |
| 6,322,538 | B1 | 11/2001 | Elbert et al. | |
| 6,689,152 | B2 * | 2/2004 | Balceta et al. | 606/200 |
| 6,743,207 | B2 | 6/2004 | Elbert et al. | |
| 6,767,340 | B2 * | 7/2004 | Willis et al. | 604/256 |
| 2007/0287962 | A1 | 12/2007 | Watanabe et al. | |

FOREIGN PATENT DOCUMENTS

| | | | |
|---|---|---|---|
| JP | 2004-261566 | A | 9/2004 |
| WO | 97/34552 | | 9/1997 |
| WO | 02066108 | A1 | 8/2002 |

* cited by examiner

*Primary Examiner* — Nicholas D Lucchesi
*Assistant Examiner* — Diva Ranade

(57) ABSTRACT

A gastrostomy tube extension device which can facilitate insertion or removal of a gastrostomy tube by making the degree of extension of the gastrostomy tube constant. A gastrostomy tube extension device used for inserting and taking out a gastrostomy tube into/from a hole formed on a patient's abdomen, the gastrostomy tube including an outer fixing member to be installed on the skin surface side, an inner fixing member installed on the inner surface side of the stomach wall, and a tube member for connecting the outer fixing member and the inner fixing member and the gastrostomy tube extension device comprising a rod and an engaging member. The rod has a rod-shaped member which can push the center of the distal end of the inner fixing member with its distal portion toward the distal end, and with a plurality of engaging step portions formed on the proximal portion. The engaging member is also provided with a lower engaging portion which can engage with an outer fixing member and an upper engaging portion which can engage one of the engaging step portions of the rod.

5 Claims, 7 Drawing Sheets

GASTROSTOMY TUBE EXTENSION DEVICE

TECHNICAL FIELD

The present invention relates to a gastrostomy tube extension device used for inserting or taking out a gastrostomy tube into/from a patient's body for feeding fluid substances such as liquid food into a stomach of a patient.

BACKGROUND ART

Hitherto, feeding of fluid substances such as liquid food or nutrient preparation using a gastrostomy tube has been carried out for persons whose capability to take food orally by their own abilities is deteriorated due to aging or diseases (hereinafter referred to as a "patient"). The gastrostomy tube includes a tube member to be installed at a hole (fistula hole) for dietary intake provided in a patient's body, an inner fixing member, often a catheter balloon, fixed to a distal portion of the tube member and installed inside of a stomach wall and an outer fixing member mounted to a proximal portion of the tube member and installed on the side of the body skin. When inserting or taking out the gastrostomy tube into/from the hole formed on the patient's body, operation for insertion and taking-out thereof is performed by a gastrostomy tube extension device, as disclosed in JP-T-2000-507134.

The gastrostomy tube extension device includes a pushing rod which can be inserted into and taken out from a fluid substance feed hole formed on the gastrostomy tube, and an engaging member including an outer fixing member engaging portion which can engage the outer fixing member of the gastrostomy tube and a finger hook on which a finger can be hooked. The inner fixing member is formed at the center of the distal end thereof with a pushing rod engaging portion with which the distal portion of the pushing rod can engage, so that the inner fixing member is elongated when the pushing rod is inserted into the fluid substance feed hole and the pushing rod engaging portion is pushed toward the distal end.

Therefore, when the pushing rod is pushed into the fluid substance feed hole while pulling the finger hook of the engaging member toward the outside (toward the proximal side of the gastrostomy tube) with fingers while the outer fixing member engaging portion of the engaging member is engaged with the outer fixing member, the inner fixing member can be elongated and narrowed. Then, since the inner fixing member in this narrowed state can pass through the hole formed on a patient's abdominal part, the gastrostomy tube can be placed in or taken out from the hole. Also, when the inner fixing member is inserted into the interior of the stomach wall and the force from the pushing rod is released by pulling out the pushing rod, the inner fixing member is brought into a swelled state by its resiliency, and hence the gastrostomy tube does not come out from the patient's body.

When inserting or taking out the aforementioned gastrostomy tube into/from a hole formed on the patient's body, it is necessary to manually maintain the position of the engaging member with respect to the pushing rod constant so that the thickness of the inner fixing member can be kept constant. In other words, with the aforementioned gastrostomy tube extension device, the operation to insert or remove the gastrostomy tube requires great skill by the user, who has to maintain the position by hand. In recent years, it has become more common for "patients" to play a greater role in their personal lives; it is now common for those requiring gastrostomy tubes for themselves or their small children to choose to maintain, and even replace, these tubes without the help of a medical doctor or nurse. This greater role of the patients, however, does require that the insertion/removal of the gastrostomy tubes be relatively uncomplicated to complete.

DISCLOSURE OF THE INVENTION

In order to solve the above-described problems, it is an object of the present invention to provide a gastrostomy tube extension device which can easily be inserted or taken out. This is achieved by fixing the degree of extension of the gastrostomy tube during the procedure.

In order to achieve the above-described object, a structural characteristic of the gastrostomy tube extension device according to the present invention is the gastrostomy tube extension device used for inserting or taking out the gastrostomy tube into/from a hole on a patient formed between a skin surface and the inner surface of a stomach wall. The gastrostomy tube includes: an outer fixing member to be installed at the hole on the skin surface side; an inner fixing member to be installed on the inner side of the stomach wall, a tube member for connecting the outer fixing member and a proximal portion of the inner fixing member, and a fluid substance feed hole extending from the outer fixing portion to the inner fixing portion.

A pushing rod formed of a rod member which can be inserted into the fluid substance feed hole, is capable of pushing the center portion of the distal end of the inner fixing member toward the distal end with the distal end portion of the rod, and is formed with a positioning engaging portion on the peripheral surface of the proximal portion.

An engaging member capable of engaging the outer fixing member and the pushing rod, is used to elongate the inner fixing portion when the pushing rod is inserted into the fluid substance feed hole and the outer fixing member, when the pushing rod is in a locked position with respect to the engaging member and the outer fixing member.

In the gastrostomy tube extension device according to the present invention configured as described above, the pushing rod is provided with a positioning engaging portion on the peripheral surface of its proximal portion, which is capable of engaging the engaging member. Therefore, when the pushing rod is inserted into the fluid feed hole of the gastrostomy tube and the outer fixing member of the gastrostomy tube and locked with the engaging member (achieved by pulling the engaging member in the proximal direction of the pushing rod), the inner fixing member is maintained in the narrowed, extended state, due to the pressure the distal end of the pushing rod exerts on the distal end of the inner fixing member. Therefore, the operator who performs the insertion or removal operation of the gastrostomy tube can concentrate on the insertion or removal operation, possibly using only one hand, without paying attention to the degree of extension of the gastrostomy tube. Consequently, insertion and removal of the gastrostomy tube into/from the hole on the patient are facilitated.

Another structural characteristic of the gastrostomy tube extension device according to the present invention is that the inner fixing member to be installed on the inner side of the stomach wall is formed of a resilient material which is elongated when the center of the distal end is pushed toward the distal direction. The distal end of the pushing rod is capable of pushing the center portion of the distal end of the inner fixing member toward the distal end, and is formed with a positioning engaging portion on the peripheral surface of the proximal portion.

The engaging member may include a joint member being connected to the gastrostomy tube and an engaging portion being capable of engaging the positioning engaging portion of the pushing rod, and elongating and narrowing the inner fixing member when the pushing rod is inserted into the fluid substance feed hole and the positioning engaging portion and the engaging portion are engaged respectively.

In this case, since the engaging member is connected to the gastrostomy tube via the joint member, the operation to connect the engaging member with the gastrostomy tube is no longer necessary, and the operation of the device is made easier.

Another structural characteristic of the gastrostomy tube extension device according to the present invention is in that one or a plurality of the positioning engaging portions are provided along the axial direction of the pushing rod. With a plurality of positioning engaging portions, the extended state of the gastrostomy tube can be changed arbitrarily by selecting the positioning engaging portion of the pushing rod to engage the second engaging portion of the engaging member as needed. Accordingly, versatility is provided, and hence one type of gastrostomy tube extension device is suitable for various body types.

Furthermore, adaptation of expansion properties or other physical properties of the gastrostomy tube can be made. For example, when inserting the gastrostomy tube into the hole on the patient, the operation is performed with the second engaging portion engaged with the positioning engaging portion which provides the smallest extension. Then, when taking out the gastrostomy tube from the hole on the patient after having placed the gastrostomy tube in the patient's body, the second engaging portion can be engaged with another positioning engaging portion. Accordingly, the operation of the gastrostomy tube can be performed with the tube in the extension state optimal for each operation.

It is further noted that the insertion/removal procedure with the present invention may be carried out using only one hand, greatly increasing the freedom of patients maintaining their gastrostomy tubes themselves.

BEST MODE FOR CARRYING OUT THE INVENTION

Hereinafter, referring to the drawings, an embodiment of the present invention will be described. FIG. 1 shows a state in which a gastrostomy tube extension device 20 according to the present invention is mounted to a gastrostomy tube 10. The gastrostomy tube 10 includes an outer fixing member 10*a*, a tube member 10*b* connected to the center of a lower end surface of the outer fixing member 10*a*, and an inner fixing member 10*c* connected to the lower end of the tube member 10*b* which are formed of polyurethane as shown in FIG. 2. In the following description, the side of the outer fixing member 10*a* is referred to as the upper side, and the side of the inner fixing member 10*c* is referred to as the lower side.

The outer fixing member 10*a* includes a main body 12 including a thick ring-shaped body provided with a vertically penetrating hole 11 at the center thereof; a cylindrical joint member 12*a* projecting downward from the center of a lower surface of the main body 12, outer holding strips 13*a*, 13*b* projecting respectively from both sides of the lower end portion on the outer peripheral surface of the main body 12, and a lid member 14 connected to a distal portion of one of the outer holding strip 13*a*. Formed on the upper end portion on an inner peripheral portion of the hole 11 formed on the main body 12 is an engaging groove 11*a* extending along the circumference thereof. Each of the outer holding strips 13*a*, 13*b* is formed into a thin plate of a substantially square shape in plan view extending horizontally from the outer peripheral surface of the main body 12 (the boundary between the outer holding strip 13*a* and the lid member 14 is a straight line).

The lid member 14 includes a band-shaped joint member 14*a* joined to the distal portion of the outer holding strip 13*a* and a plug member 15 provided at the distal end of the band-shaped joint member 14*a*. The band-shaped joint member 14*a* has flexibility and can bend so as to rotate in the vertical direction about the joint portion with respect to the outer holding strip 13*a*, able to bend at a steep angle. The distal portion of the band-shaped joint member 14*a* is formed with a wide portion 14*b* having wider width than the proximal side (at outer holding strip 13*a*), and the plug member 15 is provided on the wide portion 14*b*. The plug member 15 is provided on the wide portion 14*b* so as to face the hole 11 when the band-shaped joint member 14*a* is bent and the wide portion 14*b* is positioned on an upper surface of the main body 12.

The plug portion 15 is formed into a cylindrical shape which can be inserted into the hole 11 and is short in axial direction, and a projection 15*a* which can detachably engage the groove 11*a* of the hole 11 is provided along the circumference thereof. Therefore, the groove 11*a* and the projection 15*a* can be engaged with each other by bending the band-shaped joint member 14*a* and pressing the plug member 15 against the hole 11, and consequently, the hole 11 of the main body 12 can be clogged. Also, by pulling the wide portion 14*b* of the band-shaped joint member 14*a* forcedly upward from this state and releasing the engagement between the plug member 15 and the hole 11, the hole 11 of the main body 12 can be opened. The outer fixing member 10*a* configured as described above has a function to prevent the gastrostomy tube 10 from pulling into the stomach by being fixed to the patient's skin surface.

The upper end of the tube member 10*b* is fixed to the outer fixing member 10*a* while being inserted into the joint member 12*a*, and the interior of the tube member 10*a* defines a feed path 16 for feeding fluid substance such as liquid food. The upper end of the feed path 16 communicates with the hole 11 of the outer fixing member 10*a*, and the feed path 16 constitutes a fluid substance feed hole according to the present invention in cooperation with the hole 11 of the outer fixing member 10*a*. The tube member 10*b* is provided with elasticity, and hence is narrowed by being pulled, and returns to its original state when released from the pulled force. The tube member 10*b* has a function to prevent liquid or the like from leaking from the stomach by being positioned at a hole 33 (see FIG. 7) formed on the abdomen of the patient when it is placed in the hole 33.

The inner fixing member 10*c* includes a cylindrical joint member 17 connected to the lower end of the tube member 10*b* and an inner holding piece 18 connected to the lower end opening edge of the joint member 17. The joint member 17 is formed into a cylindrical shape which can cover the lower end portion of the outer peripheral surface of the tube member 10*b*, and is fixed to the tube member 10*b* in a state in which the lower end of the tube member 10*b* is inserted therein. The upper portion of the inner holding piece 18 is connected to the lower peripheral edge of the joint member 17 and includes a substantially dome-shaped contact portion 18*a* which comes into contact with the stomach wall when the inner fixing member 10*c* is positioned in the stomach. The lower portion of the inner holding piece 18 includes a plurality of band-shaped joint members 18*b*, in this embodiment four, joined to the lower edge of the contact portion 18*c* and a connecting portion 18*c* for connecting the distal portions of the respective joint members 18*b*.

Formed at the center portion of the upper surface of the contact portion 18*a* is a hole which communicates with the feed path 16 of the tube member 10*b*. The hole constitutes the fluid substance feed hole together with the hole 11 of the outer fixing member 10*a* and the feed path 16. The center portion of the upper surface of the contact portion 18*a* with which the stomach wall comes into contact is formed into a flat shape. The plurality of joint members 18*b* are provided at regular intervals around the circumference at the lower end of the contact portion 18*a*, extend separately axially from the lower edge of the contact portion 18*a* downward respectively, and then are converged at a lower position of the center axis of the tube member 10*b* to constitute the connecting portion 18*c* and thus are fixed together.

In other words, the connecting portion 18*c* connects the respective joint members 18*b* with each other by joining the lower end portions of the respective joint members 18*b*, and is positioned at a lower location of the center axis of the tube member 10*b*. Therefore, the inner holding piece 18 is formed into substantially a spherical shape as a whole with the pairs of opposing joint members 18*b*, 18*b*, and the outline of the contact portion 18*a* forming circles respectively.

The contact portion 18*a* and the respective joint members 18*b* are formed of soft resilient material having flexibility, and are maintained in a substantially spherical shape as a whole by the resiliency thereof as shown in FIG. 2 in a normal state. However, when the connecting portion 18*c* is pressed downward, it is expanded to a straight narrow state. In comparison with the sub-portions of the contact portion 18*a* above the respective joint members 18*b*, the sub-portions other than the above-described sub-portions are thinner.

Therefore, the contact portion 18*a* is constructed of the portion extending from the joint members 18*b* and the thinned portions therebetween, and hence when the connecting portion 18*c* is pulled downward, it is folded to a specific shape and is easily narrowed. The connecting portion 18*c* is formed at the center with a hole, and an engaging portion 19 of a short cylindrical shape is fixed to this hole. The engaging portion 19 is formed at the center thereof with a hole 19*a* for positioning the distal portion of a rod (see FIG. 3) 21 described later. The inner fixing member 10*c* configured as described above has a function to be fixed to the inner surface of the stomach wall of the patient and prevents the gastrostomy tube 10 from leaving the patient's body.

The gastrostomy tube extension device 20 includes a rod 21 used as the pushing rod, and an engaging member 22 according to the present invention as shown in FIG. 3. The rod 21 is provided with a main body 21*a* formed of a rod-shaped member possibly formed of stainless steel, and a holding portion 21*b* possibly formed of plastic. The main body 21*a* is provided with a pushing portion 23, possibly formed of plastic, attached at the distal end thereof. The pushing portion 23 includes a secured portion 23*a* fixed to the main body 21*a* which covers the peripheral surface of the lower end portion of the main body 21*a* and a push-insertion piece 23*b* extending downward from the lower end of the secured portion 23*a*.

The outer diameter of the secured portion 23*a* is set to be larger than the diameter of the hole 19*a* of the engaging portion 19, and the diameter of the push-insertion piece 23*b* is set to be smaller than the diameter of the hole 19*a*. Therefore, when the rod 21 is inserted downward from the hole 11 of the gastrostomy tube 10, the push-insertion piece 23*b* is inserted into the hole 19*a*, and the secured portion 23*a* is located in such a manner that its lower surface contacts the upper surface of the engaging portion 19. Accordingly, when the rod 21 is pressed downward into the gastrostomy tube 10, the inner fixing member 10*c* extends and narrows.

A cylindrical portion 24 configured integrally with the holding portion 21*b* is formed on the upper portion of the main body 21*a* and below the holding portion 21*b* so as to cover the entire circumference of the main body 21*a*, and a plurality of engaging step portions 24*a* as the positioning engaging portions of the present invention are formed on the outer peripheral surface thereof. Each engaging step portion 24*a* is a ring-shaped projection possibly of substantially triangular shape in vertical cross-section formed on the peripheral surface of the cylindrical portion 24 all along the circumference thereof, and possibly five of these engaging step portions 24*a* may be formed at regular intervals along the axial direction of the cylindrical portion 24. The upper surface of the holding portion 21*b* is ideally formed into a curved surface depressed into an arcuate shape for allowing the operator's hand or finger, in particular, the thumb to fit for operation.

The engaging member 22 is formed into a shape as shown in FIG. 3 possibly by machining a stainless steel plate, and includes a lower engaging portion 25 as the first engaging portion of the present invention, and an upper engaging portion 26 as the second engaging portion of the present invention. The lower engaging portion 25 and the upper engaging portion 26 are connected by a joint strip 27 of a vertically elongated rectangular plate shape. The lower engaging portion 25 includes a holding strip 25*a* of substantially U-shape in plan view which is formed from the lower end of the joint strip 27, extending horizontally toward the near side of the drawing and orthogonally to the joint strip 27, and a pair of claw portions 25*b* provided in parallel with the holding strip 25*a* so as to extend from the both sides of the lower end portion of the joint strip 27, orthogonally to the joint strip 27 and at a distance from the holding strip 25*a*. The inside of the substantially U-shape of the holding strip 25*a* is formed into a recess which can accommodate the joint member 12*a* of the outer fixing member 10*a* and the distance between the holding strip 25*a* and the claw portion 25*b* is set to a distance which can clamp the outer holding strips 13*a*, 13*b*.

The upper engaging portion 26 is formed so as to extend from the upper end of the joint strip 27 horizontally toward the near side of the drawing and orthogonally to the joint strip 27, and is configured by a laterally elongated part extending from both sides of the joint strip 27. The length of the upper engaging portion 26 in the fore-and-aft direction is set to be short, relative to the length of the holding strip 25*a*, and is formed with an engaging recess 26*a* in the front center which can engage the respective engaging step portions 24*a*. A pair of projections 26*b* for preventing the engagement with the engaging step portion 24*a* from being released project downward at both sides of the engaging recess 26*a* of the front portion of the upper engaging portion 26. In addition, laterally both side portions of the upper engaging portion 26 may be curved downwardly so as to facilitate operation performed with the operator's hand hooked therewith, and the distal portion of the holding strip 25*a* may be curved upward so as to prevent engagement with the outer holding strips 13*a*, 13*b* from being released.

In this structure, in order to place the gastrostomy tube 10 in the hole 33 formed on the abdominal part of the patient, the wide portion 14*b* is pulled to open the hole 11 of the outer fixing member 10*a* and the rod 21 is inserted from the hole 11 toward the lower side of the tube member 10. Then, the push-insertion piece 23*b* of the rod 21 is aligned with the engaging portion 19 of the inner fixing member 10*c* and pushed into the hole 19*a*. Subsequently, the engaging member 22 is assembled to the gastrostomy tube 10 and the rod 21 in a state in which the outer holding strips 13*a*, 13*b* of the gastrostomy tube 10 in this state are clamped between the holding strip 25*a* and the claw portions 25*b* and the main body 21*a* is positioned in the engaging recess 26*a* to obtain the state shown in FIG. 1 or FIG. 4 (the direction of the gastrostomy tube 10 is different from FIG. 1).

Subsequently, in a state in which the operator holds down the upper surface of the holding portion 21*b* by hand to prevent the push-insertion piece 23*b* from coming apart from the hole 19*a*, the operator hooks his fingers with the lower surface of the upper engaging portion 26 and pulls the engaging member 22 upward so that the edge of the engaging recess 26*a* is engaged with the predetermined engaging step portion 24*a*, for example, the engaging step portion 24*a* located at the center. Accordingly, as shown in FIG. 5, the inner fixing member 10*c* extends straight and is narrowed, and hence the tube member 10*b* and the inner fixing member 10*c* take a shape similar to one single rod.

In this case, not only the inner fixing member 10*c*, but also the tube member 10*b* is brought into an extended state. The gastrostomy tube 10 and the gastrostomy tube extension device 20 are assembled in a state in which the outer holding strips 13*a*, 13*b* are prevented from separating from the holding strip 25*a* by the curved portion at the distal end of the holding strip 25*a*, and the engaging step portion 24*a* of the rod 21 is prevented from separating from the engaging recess 26*a* by the projection 26*b* as shown in FIG. 6.

Subsequently, the gastrostomy tube 10 is inserted into the hole 33 formed on an abdominal wall 31 and a stomach wall 32 of the patient shown in FIG. 7 in the extended state as shown in FIG. 5. When the inner fixing member 10*c* enters the patient's stomach, the operator pulls the engaging member 22 upward while hooking his/her finger on the lower surface of the upper engaging portion 26, and separates the engaging recess 26*a* from the engaging step portion 24*a* as well as separating the holding strip 25*a* and the claw portion 25*b* from the outer holding strips 13*a*, 13*b*, whereby the engaging member 22 is removed from the gastrostomy tube 10. Then, the operator pulls out the rod 21 from the gastrostomy tube 10, and then bends the band-shaped joint member 14*a* to press the plug member 15 against the hole 11 to clog the hole 11 of the main body 12.

Accordingly, as shown in FIG. 7, the inner fixing member 10*c* returns to the original substantially spherical shape due to its resiliency, and the upper surface of the contact portion 18*a* comes into contact with the inner surface of the stomach wall 32. The tube member 10*b* is also restored to the original state. Consequently, the gastrostomy tube 10 is prevented from leaving the hole 33, and maintains the state of being attached to the abdomen of the patient. The portions of the abdominal wall 31 and the stomach wall 32 near the hole 33 are fixed so as not to be displaced in position from each other. In this case, it is preferable to leave a slight gap between the surface of the abdominal wall 31 and the lower surface of the outer fixing member 10*a*, so that a slight degree of freedom is provided between the gastrostomy tube 10 and the hole 33.

Then, when feeding fluid substance such as liquid food or nutrient preparation to the patient, the hole 11 of the outer fixing member 10*a* is opened, and a fluid feed tube (not shown) is connected to the hole 11. In this state, the fluid substance is fed from an opening at the end of the fluid feed tube into the fluid feeding tube. Consequently, the fluid substance is fed from the fluid feed tube via the hole 11 and the feed path 16 into the patient's stomach. In this case, the fluid substance coming out from the lower end opening of the tube member 10*b* passes from inside the inner fixing member 10*c* through the respective joint members 18*b* into the stomach. After use, the operator removes the fluid feed tube from the outer fixing member 10*a* and closes the hole 11.

When a physical property of the gastrostomy tube 10 is changed, such as expansion after a certain period of use, and hence replacement is needed, the rod 21 and the engaging member 22 are mounted to the gastrostomy tube 10 in the abdomen of the patient as in the aforementioned operation. In this case, when the gastrostomy tube 10 has expanded, the engaging recess 26*a* of the engaging member 22 is engaged at the uppermost engaging step portion 24*a* or the second engaging step portion 24*a* from the top. Accordingly, the inner fixing member 10*c* can be brought into a narrow width which is suitable for its removal. The gastrostomy tube 10 is taken out from the patient's body together with the rod 21 and the engaging member 22, with the inner fixing member 10*c* narrowed as described above. Then, the new gastrostomy tube 10 is attached to the patient's body as in the aforementioned operation.

As described above, the gastrostomy tube extension device 20 according to this embodiment includes the rod 21 and the engaging member 22. Then, the rod 21 is provided at the lower end thereof with the push-insertion piece 23*b* which is engageable with the hole 19*a* of the engaging portion 19 provided on the gastrostomy tube 10, and on the peripheral surface of the upper portion of the rod 21 with the engaging step portions 24*a*. The engaging member 22 is provided with the lower engaging portion 25 engageable with the outer holding strips 13*a*, 13*b* of the gastrostomy tube 10 and the upper engaging portion 26 engageable with the engaging strips 24*a* of the rod 21.

Therefore, when the rod 21 is inserted into the gastrostomy tube 10, and the outer holding strips 13*a*, 13*b* are engaged with the lower engaging portion 25, by pulling the engaging member 22 upward and causing the upper engaging portion 26 to engage with the predetermined engaging step portion 24*a*, the inner fixing member 10*c* is maintained in a thinned state. Therefore, the operator can concentrate on the insertion or removal operation without paying attention to the degree of extension of the gastrostomy tube 10. Consequently, insertion and removal of the gastrostomy tube 10 into/from the hole 33 on the patient are made easy.

The distal portion of the holding strip 25*a* of the lower engaging portion 25 is bent upward and hence it is hard for the lower engaging portion 25 to separate from the outer holding strips 13*a*, 13*b*, and a pair of the projections 26*b* are formed at the ends of the opening of the engaging recess 26*a* on the front portion of the upper engaging portion 26, so that it is hard for the upper engaging portion 26 to separate from the engaging strips 24*a* of the rod 21. Therefore, the gastrostomy tube extension device 20 maintains stable extension of the gastrostomy tube 10, never separating from the gastrostomy tube 10.

Also, the engaging step portions 24*a* may be formed at regular intervals, and the length of the gastrostomy tube 10 can be extended by stages. Accordingly, versatility is provided, and hence one type of gastrostomy tube extension device 20 may be sufficient for insertion and removal of the various gastrostomy tubes. Also, since the engaging step portion 24*a* to be engaged with the engaging recess 26*a* may be selected according to the change in the expansion or other physical properties of the gastrostomy tube 10, the operation in the optimal state is achieved.

The gastrostomy tube extension device according to the present invention is not limited to the aforementioned embodiment, and may be changed as needed within the technical scope of the present invention. For example, although the gastrostomy tube 10 and the engaging member 22 in the aforementioned embodiment are separate members, they may be formed integrally. In the aforementioned embodiment, although five engaging step portions 24*a* are formed on the rod 21, the number of the engaging step portions 24*a* may be plural of four or smaller, or six or larger, or may be single. The joint members 18*c* may also vary in number or shape, even perhaps being formed into one member, within the scope of this disclosure.

In addition, it is also possible to form the engaging step portion 24*a* to have an angular portion having a ridge line 34*b* at the center like the engaging step portion 34*a* formed into the cylindrical portion 34 shown in FIG. 8 instead of a smoothly curved shape. This arrangement further ensures engagement with respect to the engaging recess 26*a*. Further, instead of a ring shape, the engaging step portion may be formed of a projection projecting from a predetermined position on the cylindrical portion or may be formed of a recess with which the upper engaging portion 26 can engage. Also, the shapes or materials of other portions constituting the gastrostomy tube 10 and the gastrostomy tube extension device 20 may also be changed as needed.

Figure 1:
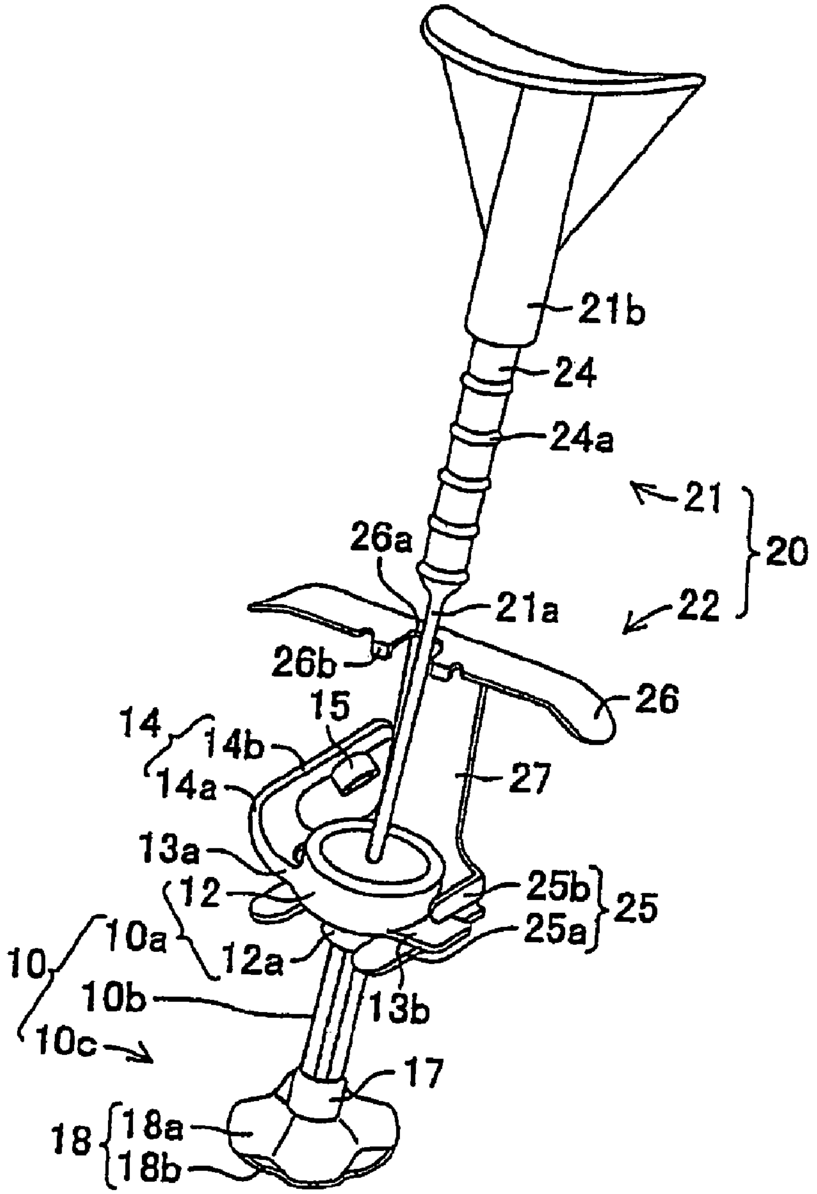
FIG. 1 is a perspective view showing a state in which a gastrostomy tube extension device according to a first embodiment of the present invention is mounted to a gastrostomy tube.
Figure 2:
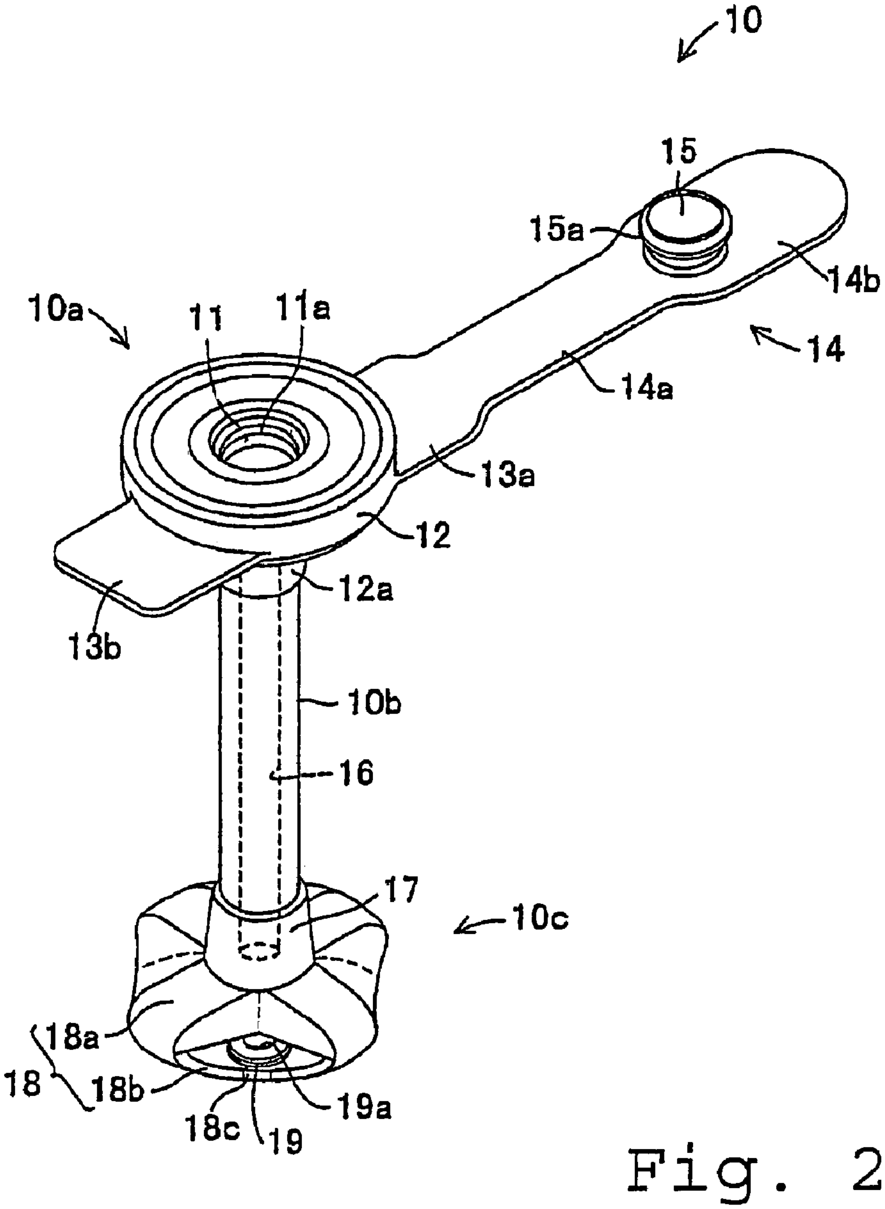
FIG. 2 is a perspective view of the gastrostomy tube.
Figure 3:
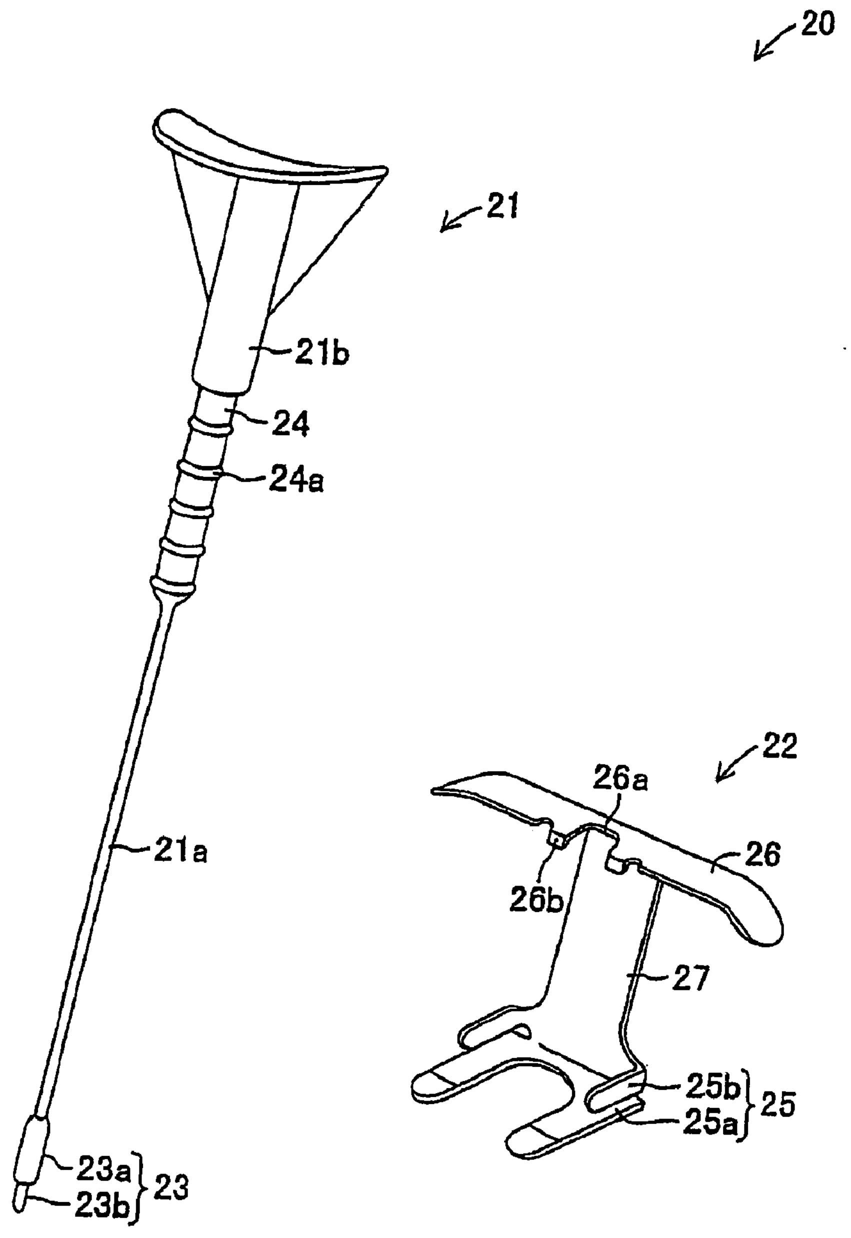
FIG. 3 is a perspective view of the gastrostomy tube extension device.
Figure 4:
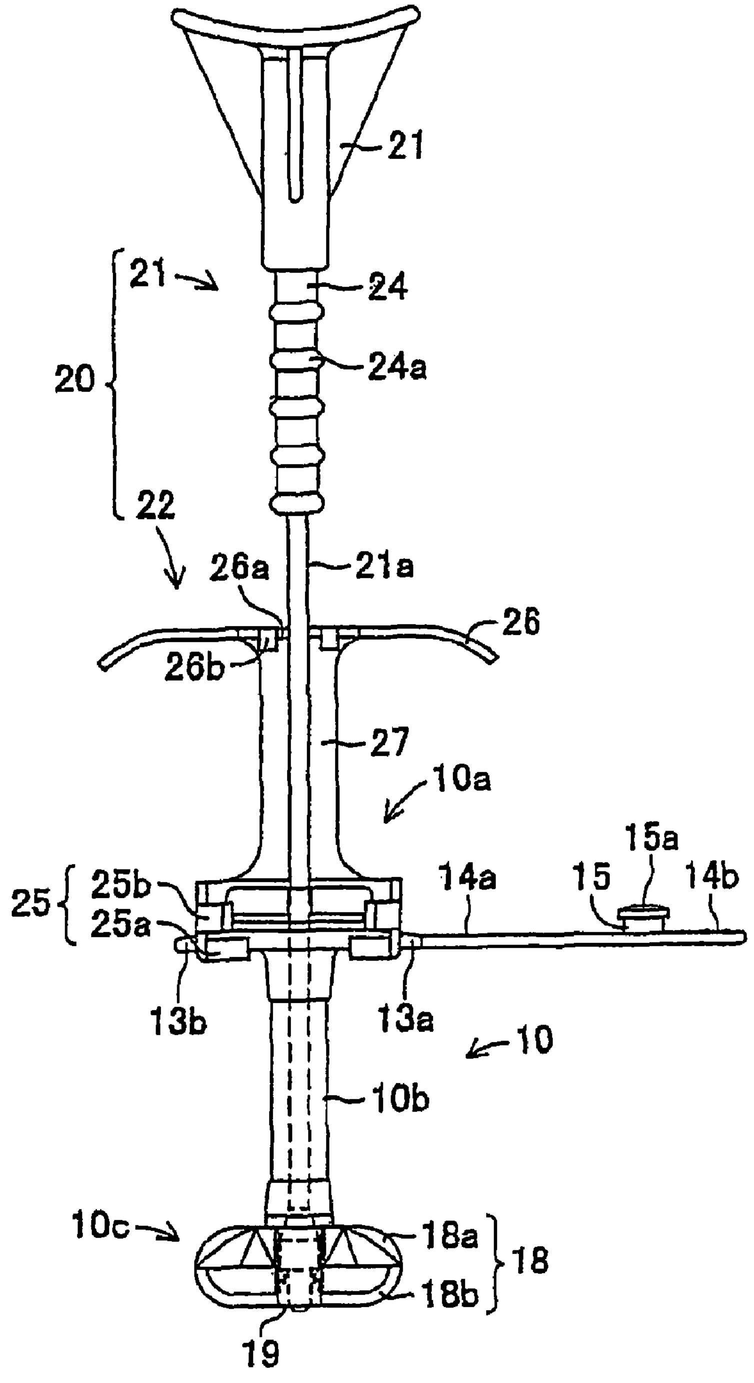
FIG. 4 is a front view showing a state in which the gastrostomy tube extension device is mounted to the gastrostomy tube.
Figure 5:
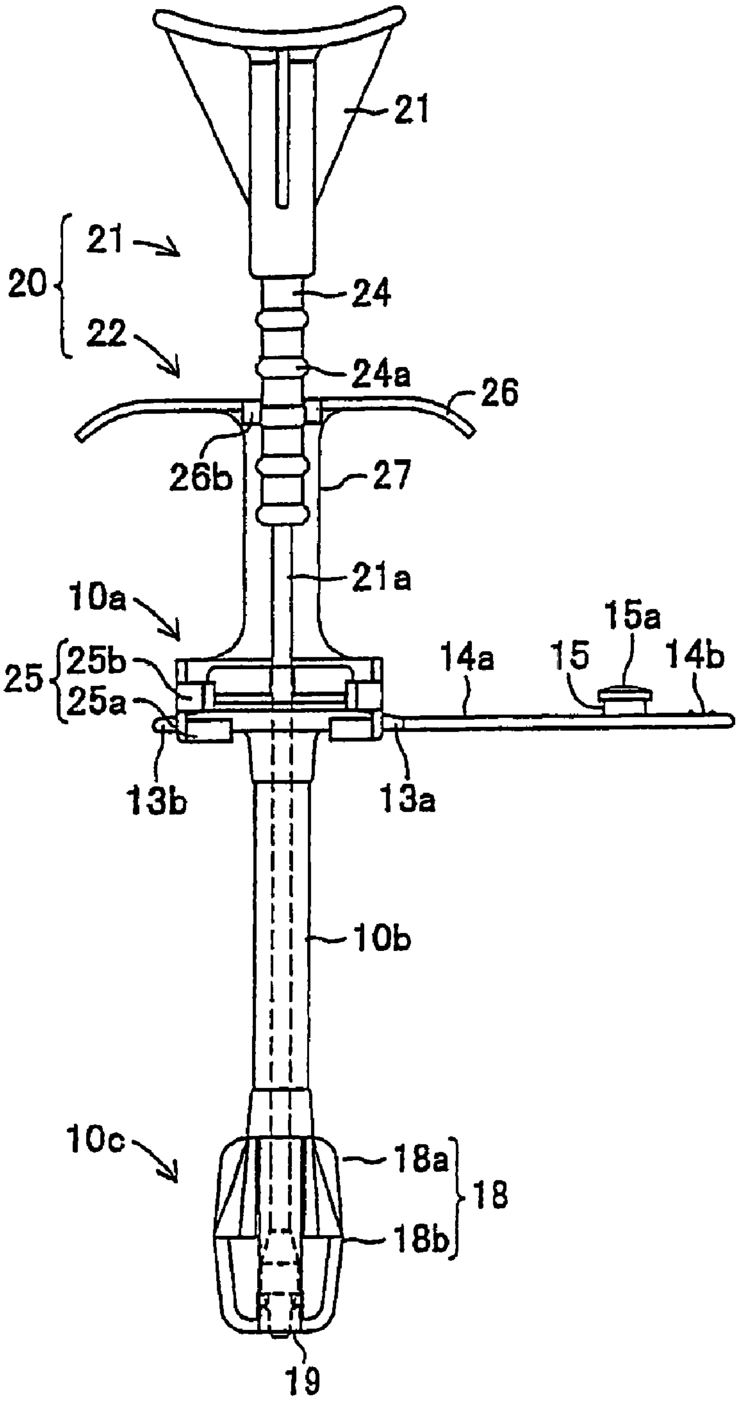
FIG. 5 is a front view showing a state in which the gastrostomy tube is extended by the gastrostomy tube extension device.
Figure 6:
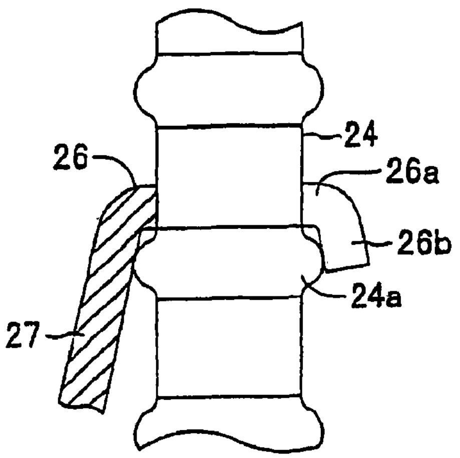
FIG. 6 is a cross-sectional view showing a state in which an engaging step portion and an engaging recess are engaged.
Figure 7:
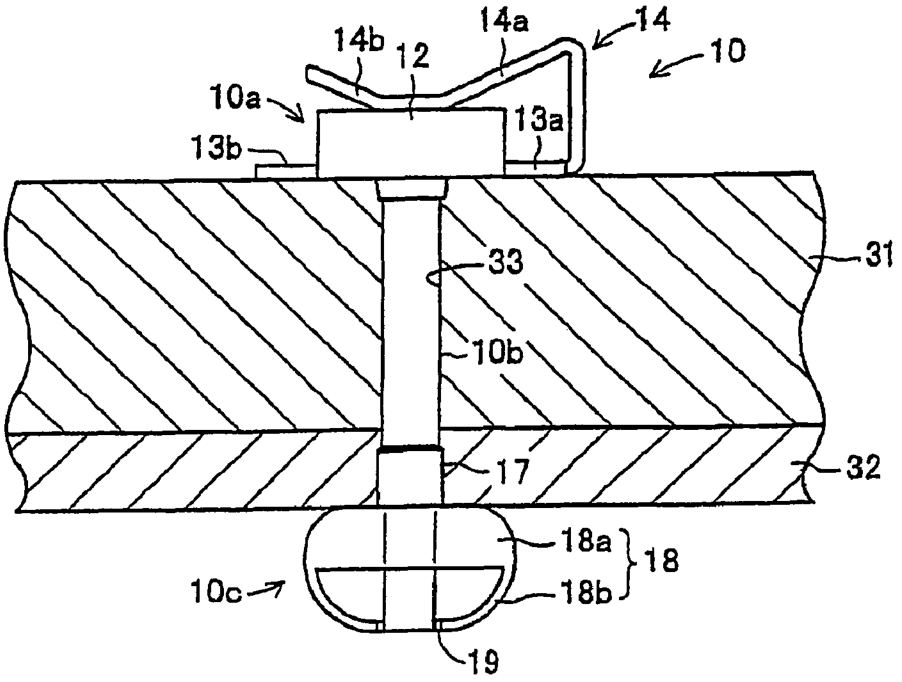
FIG. 7 is a cross-sectional view showing a state in which the gastrostomy tube is placed in the patient's body.
Figure 8:
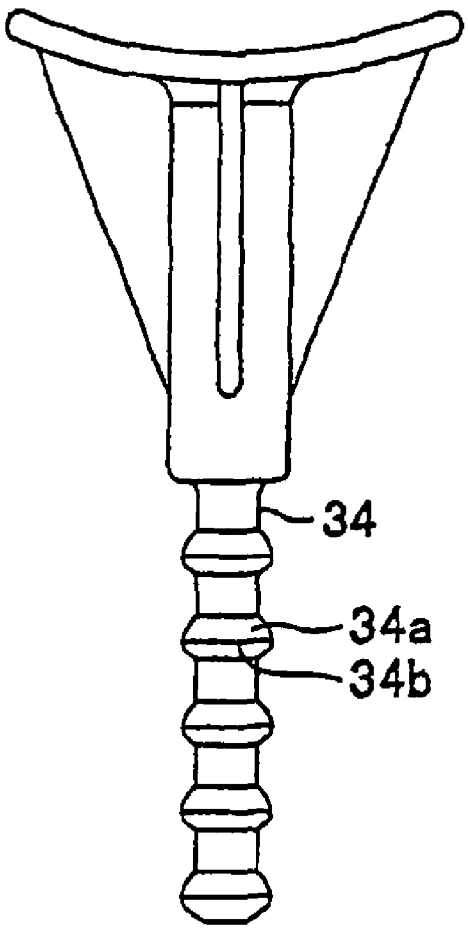
FIG. 8 is a front view showing a modification of the engaging step portion.

The invention claimed is:

1. A gastrostomy tube extension device used for inserting or taking out a gastrostomy tube into/from a hole on a patient formed between the skin surface and the inner surface of a stomach wall, the gastrostomy tube comprising an outer fixing member to be installed at the hole of the patient on the skin surface side, an inner fixing member to be installed on the inner side of the stomach wall which is formed of resilient material which is elongated and narrowed when the center of the distal end thereof is pushed toward the distal end, a tube member for connecting the outer fixing member and the proximal portion of the inner fixing member, and a fluid substance feed hole extending from the outer fixing portion to the inner fixing portion, said extension device comprising:

a pushing rod comprising a rod member which can be inserted into the fluid substance feed hole, is capable of pushing the center portion of the distal end of the inner fixing member toward the distal end with the distal end portion thereof, and is formed with a positioning engaging portion on the peripheral surface of a proximal portion of the pushing rod; and an engaging member including a first engaging portion which is capable of engaging the outer fixing member, and a second engaging portion which is capable of engaging the positioning engaging portion of the pushing rod, the engaging member elongating and narrowing the inner fixing portion when the pushing rod is inserted into the fluid substance feed hole and the outer fixing member and the first engaging portion, and the positioning engaging portion and the second engaging portion are respectively engaged with each other, and wherein the positioning engaging portion comprises at least one engaging step portion that is ring-shaped.

2. A gastrostomy tube extension device used for inserting or taking out a gastrostomy tube into/from a hole on a patient formed between a skin surface and an inner surface of a stomach wall of the patient, the gastrostomy tube comprising an outer fixing member to be installed at the hole on the skin surface side, an inner fixing member to be installed on the inner side of the stomach wall and which is formed of resilient material which is elongated and narrowed when the center of the distal end thereof is pushed toward the distal end, a tube member for connecting the outer fixing member and the proximal portion of the inner fixing member, and a fluid substance feed hole extending from the outer fixing portion to the installed on the inner side of the stomach wall which is formed of resilient material which is elongated and narrowed when the center of the distal end thereof is pushed toward the distal end; a tube member for connecting the outer fixing member and the proximal portion of the inner fixing member; and a fluid substance feed hole extending from the outer fixing member to the inner fixing member, and wherein the positioning engaging portion comprises at least one engaging step portion that is ring-shaped.

3. The gastrostomy tube extension device according to claim 1 wherein the at least one engaging step portions are formed at regular intervals.

4. The gastrostomy tube extension device according to claim 2 wherein the at least one engaging step portions are formed at regular intervals.

5. A gastrostomy tube extension device used for inserting or taking out a gastrostomy tube into/from a hole on a patient formed between the skin surface and the inner surface of a stomach wall, the gastrostomy tube comprising an outer fixing member to be installed at the hole of the patient on the skin surface side, an inner fixing member to be installed on the inner side of the stomach wall which is formed of resilient material which is elongated and narrowed when the center of the distal end thereof is pushed toward the distal end, a tube member for connecting the outer fixing member and the proximal portion of the inner fixing member, and a fluid substance feed hole extending from the outer fixing portion to the inner fixing portion, said extension device comprising:

a pushing rod comprising a rod member which can be inserted into the fluid substance feed hole, is capable of pushing the center portion of the distal end of the inner fixing member toward the distal end with the distal end portion thereof, and is formed with a positioning engaging portion on the peripheral surface of a proximal portion of the pushing rod; and an engaging member including a first engaging portion which is capable of engaging the outer fixing member, and a second engaging portion which is capable of engaging the positioning engaging portion of the pushing rod, the engaging member elongating and narrowing the inner fixing portion when the pushing rod is inserted into the fluid substance feed hole and the outer fixing member and the first engaging portion, and the positioning engaging portion and the second engaging portion are respectively engaged with each other, and wherein the positioning engaging portion comprises at least one engaging step portion that is formed to have an angular portion having a ridge line at the center.

* * * * *